US006781522B2

(12) United States Patent
Sleva et al.

(10) Patent No.: US 6,781,522 B2
(45) Date of Patent: Aug. 24, 2004

(54) PORTABLE STORAGE CASE FOR HOUSING A MEDICAL MONITORING DEVICE AND AN ASSOCIATED METHOD FOR COMMUNICATING THEREWITH

(75) Inventors: Michael Zigmund Sleva, Charlotte, NC (US); Kevin James Schimelfenig, Huntersville, NC (US); Kyle McGeever Schimelfenig, Huntersville, NC (US)

(73) Assignee: Kivalo, Inc., Huntersville, NC (US)

( * ) Notice: Subject to any disclaimer, the term of this patent is extended or adjusted under 35 U.S.C. 154(b) by 518 days.

(21) Appl. No.: 09/935,311

(22) Filed: Aug. 22, 2001

(65) Prior Publication Data

US 2003/0038047 A1 Feb. 27, 2003

(51) Int. Cl.⁷ ............................................... G08C 17/00
(52) U.S. Cl. .................... 340/870.1; 361/683; 361/724; 361/728; 600/372; 706/569; 706/570
(58) Field of Search ........................ 340/870.1; 361/683, 361/685, 724, 728; 206/570, 569, 718; 600/504, 372

(56) References Cited

U.S. PATENT DOCUMENTS

| | | |
|---|---|---|
| 3,786,510 A | 1/1974 | Hodges |
| 4,429,793 A | 2/1984 | Ehmann |
| 4,770,328 A | 9/1988 | Dickhudt et al. |
| 4,848,587 A | 7/1989 | Nipp |
| 4,974,607 A | 12/1990 | Miwa |
| 5,307,263 A | 4/1994 | Brown |
| 5,348,347 A | 9/1994 | Shink |
| 5,371,687 A | 12/1994 | Holmes, II et al. |
| 5,423,404 A | 6/1995 | Shaw |
| 5,594,906 A | 1/1997 | Holmes, II et al. |
| 5,678,571 A | 10/1997 | Brown |
| 5,730,654 A | 3/1998 | Brown |
| 5,832,448 A | 11/1998 | Brown |
| 5,865,314 A | 2/1999 | Jacober |
| 5,897,493 A | 4/1999 | Brown |
| 5,899,855 A | 5/1999 | Brown |
| 5,913,310 A | 6/1999 | Brown |

(List continued on next page.)

FOREIGN PATENT DOCUMENTS

| | | |
|---|---|---|
| DE | 196 02 299 A | 7/1997 |
| DE | 197 50 009 C | 9/1999 |
| WO | WO 00/18293 A1 | 4/2000 |
| WO | WO 00/28460 A | 5/2000 |
| WO | WO 00/32098 A1 | 6/2000 |
| WO | WO 00/33236 A1 | 6/2000 |
| WO | WO 01/37174 A1 | 5/2001 |

OTHER PUBLICATIONS

*A Guessing Game to Rally the Diabetic Child*, C. Herold, New York Times, Jul. 26, 2001.

Primary Examiner—Albert K. Wong
(74) Attorney, Agent, or Firm—Alston & Bird LLP

(57) ABSTRACT

A portable storage case for housing a medical monitoring device is provided that facilitates communications with the medical monitoring device while the portable storage case is in transport. The portable storage case may also store the accessories required for the tests and a portable computing device for receiving additional data relating to the various activities of the patient. In order to communicate with the medical monitoring device, the portable storage case may include an integral data connector disposed in a predetermined positional relationship with respect to the medical monitoring device. As such, communication may be established between the integral data connector and a corresponding data connector carried by the medical monitoring device such that data collected by the medical monitoring device may be accessed, such as by being downloaded, once the medical monitoring device is disposed within the case.

31 Claims, 5 Drawing Sheets

U.S. PATENT DOCUMENTS

| | | | |
|---|---|---|---|
| 5,918,603 A | 7/1999 | Brown |
| 5,931,791 A | 8/1999 | Saltzstein et al. |
| 5,933,136 A | 8/1999 | Brown |
| 5,960,403 A | 9/1999 | Brown |
| 5,985,559 A | 11/1999 | Brown |
| 5,997,476 A | 12/1999 | Brown |
| 6,047,752 A | 4/2000 | Southwick |
| 6,101,478 A | 8/2000 | Brown |
| 6,151,586 A | 11/2000 | Brown |
| 6,161,095 A | 12/2000 | Brown |
| 6,167,362 A | 12/2000 | Brown et al. |
| 6,168,563 B1 | 1/2001 | Brown |
| 6,186,145 B1 | 2/2001 | Brown |
| 6,190,326 B1 | 2/2001 | McKinnon et al. |
| 6,200,264 B1 | 3/2001 | Satherley et al. |
| 6,210,272 B1 | 4/2001 | Brown |
| D441,867 S | 5/2001 | Belisle et al. |
| 6,240,393 B1 | 5/2001 | Brown |
| 6,245,013 B1 | 6/2001 | Minoz et al. |
| 6,246,992 B1 | 6/2001 | Brown |
| 6,248,065 B1 | 6/2001 | Brown |
| 6,264,029 B1 | 7/2001 | Motson |
| 6,270,455 B1 | 8/2001 | Brown |
| 2001/0047125 A1 | 11/2001 | Quy |
| 2002/0002326 A1 | 1/2002 | Causey, III et al. |
| 2002/0068858 A1 | 6/2002 | Braig et al. |
| 2003/0065536 A1 | 4/2003 | Hansen et al. |

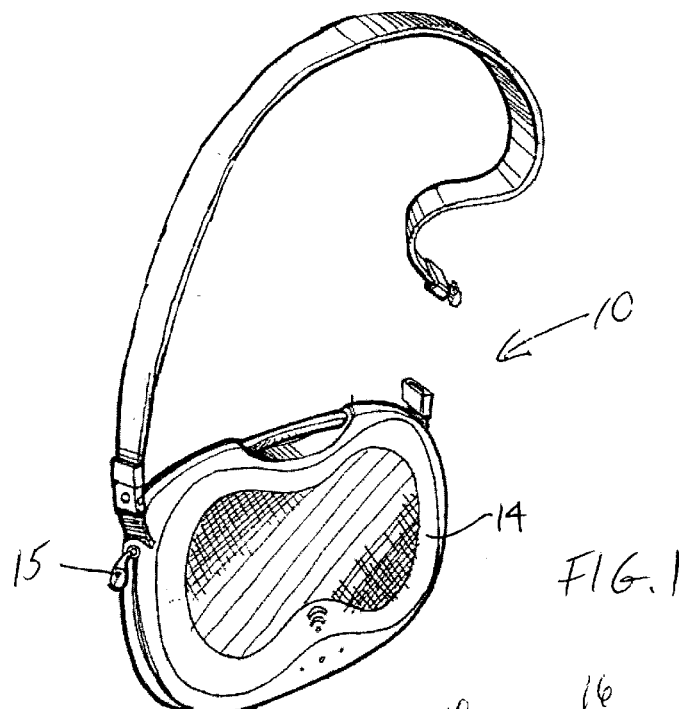
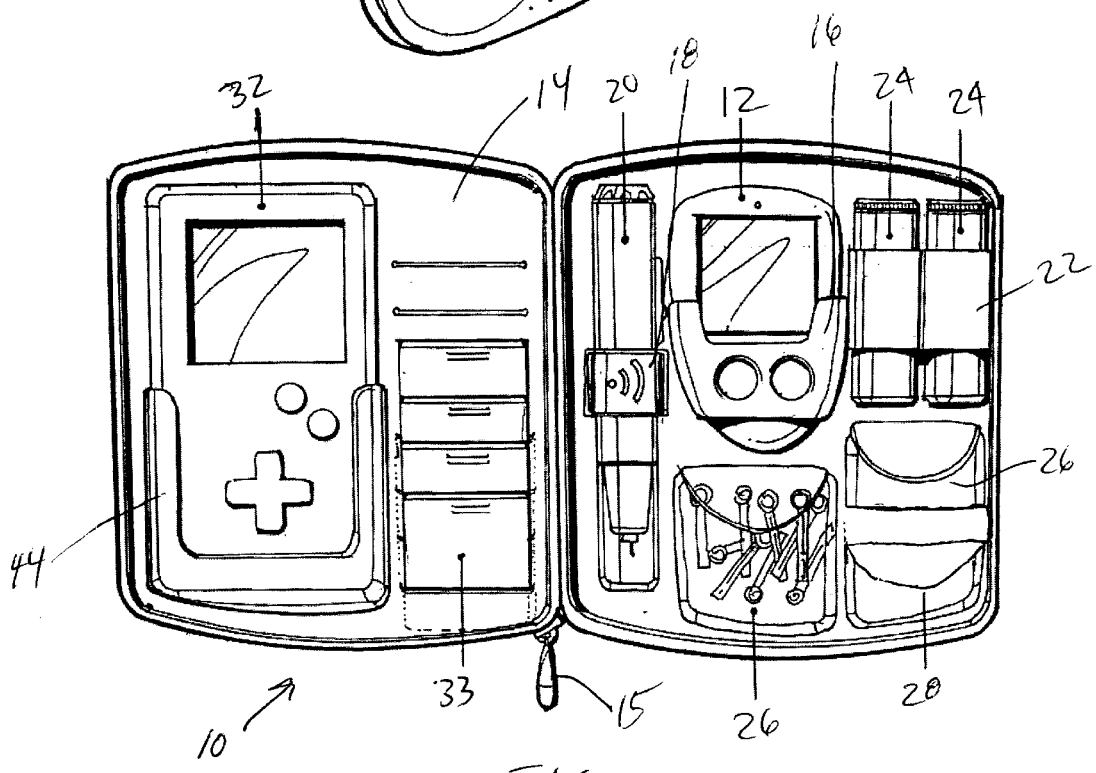

PORTABLE STORAGE CASE FOR HOUSING A MEDICAL MONITORING DEVICE AND AN ASSOCIATED METHOD FOR COMMUNICATING THEREWITH

FIELD OF THE INVENTION

The present invention relates generally to a portable storage case for housing a medical monitoring device and, more particularly, to a portable storage case and an associated method for housing a medical monitoring device and for facilitating communication therewith.

BACKGROUND OF THE INVENTION

In addition to the periodic examination by a physician in the physician's office, it is oftentimes desirable to monitor the medical condition of a patient on a more frequent basis including at times during which the patient is otherwise engaged in normal day-to-day activities. For example, diabetic patients must generally test their blood sugar several times a day. If the blood sugar readings are either abnormally high or abnormally low, the patient can then take appropriate remedial action in order to bring their blood sugar back within the normal range. For example, the patient may administer an insulin shot, drink a glass of orange juice, eat a candy bar or rest for a while in order to allow their blood sugar to return to normal. As another example, patients suffering from various types of heart conditions may need to monitor their blood pressure, pulse rate and the like on a fairly frequent basis throughout the day such that a patient can identify instances in which they should rest and/or relax in order to maintain their blood pressure, pulse and the like at normal levels.

Patients who are both knowledgeable of their medical condition and diligent in monitoring their medical condition can generally identify instances in which remedial action is desirable and then decide upon and institute the appropriate remedial action, such as by adjusting their medication, diet and/or their level of exertion, on an ongoing basis such that they remain in a relatively stable condition. However, a number of patients are either incapable of or unwilling to monitor their medical condition, and then decide upon and institute the appropriate remedial action in order to remain in a relatively stable condition.

For example, a number of children are afflicted with juvenile diabetes. Like adults who are diabetic, children stricken with juvenile diabetes must test their blood sugar several times during a day and must adjust their medication, diet and/or level of exertion in order to maintain their blood sugar at a relatively normal level since failure to maintain their blood sugar at a relatively normal level may cause the child to suffer a diabetic seizure and, over an extended period of time, may lead to blindness, amputation, strokes and even death. Notwithstanding the severe consequences of failing to maintain their blood sugar at a relatively normal level, children oftentimes become preoccupied with other activities and fail to test their blood sugar as frequently as desired. Even in instances in which a child does test his or her blood sugar on a frequent basis, the child may lack the knowledge and experience that is required to determine the remedial steps that should be taken in order to return their blood sugar to a normal level. In addition, a number of elderly patients may be either unable or unwilling to repeatedly monitor their medical condition and to make an educated decision as to whether remedial action is necessary and, if so, what type of remedial action is required in order to remain in a relatively stable condition.

In these situations in which the patient, such as a child or an elderly person, is either unable or unwilling to gather the medical data, interpret the medical data and/or take appropriate remedial actions, a physician, a nurse or other caregiver must intervene in order to remedy the situation. Unfortunately, except in instances in which the patient is hospitalized or is a resident at a nursing home, an extended care facility or the like, the patient is generally remote from the physician, nurse or other caregiver.

In order to obtain the assistance of a physician, a nurse or other caregiver, the patient may be required to visit the physician's office on both a very frequent basis as well as in instances in which abnormal medical data is detected. Even in instances in which the patient promptly goes to the physician's office following the detection of abnormal medical data, some time delay will occur between the detection of the abnormal data and the conference between the patient and the physician. During this time delay, the condition of the patient may worsen since the patient may otherwise fail to take proper remedial action until they have consulted with their physician. This time delay is obviously further exacerbated in instances in which the patient fails to identify an abnormal situation. In addition to the potentially harmful effects to the patient's health occasioned by the failure to remedy the situation until after visiting the physician's office, the patient will incur substantial costs for each office visit, thereby potentially discouraging the patient from visiting the physician as often as otherwise desirable in a misguided attempt to reduce medical costs.

In order to properly treat the patient's condition and to identify the cause of the problem, a physician oftentimes would like to have additional medical data from earlier in the day, the prior day or even before. As such, a variety of monitors have been developed for monitoring a number of medical conditions that include memory devices for storing the medical data for some period of time such that a physician can download the medical data during the patient's visit to the physician's office in order to review at least the recent history of the patient. For example, blood glucose meters have been developed for monitoring the blood sugar of a patient and for storing the measured values obtained over a period of time, typically with a time and date stamp defining when the blood sugar reading was obtained. Likewise, heart monitors having memory devices have been developed and are worn by patients to monitor and store their pulse rate, their heart rhythm and the like.

In addition to a monitor, the patient oftentimes require the number of accessories. For example, in order to monitor the blood sugar of a diabetic patient, the patient not only must carry a blood glucose meter, but also must generally carry a number of lancets and a lancing device. In addition, a diabetic patient must also typically carry a number of test strips as well as a vial of calibration liquid. As such, carrying cases have been developed for storing the blood glucose meter and the testing accessories. Some patients, however, carry the various accessories loosely in their briefcase, purse, backpack or the like and, as a result may have difficulty readily locating all of the necessary accessories in order to test their blood sugar since the briefcase, purse, backpack or the like generally includes a large number of other items. In addition, the accessories must generally be quite clean in order to attain accurate readings. As such, storage of the accessories in a loose manner in a briefcase, purse, backpack or the like may undesirably soil or otherwise contaminate the accessories and therefore somewhat decrease the reliability of the resulting readings. In addition, for those tests that draw blood, such as tests of a patient's blood sugar, the accessories, such as the lancets and test strips, that are utilized for the test may need to be stored and disposed of in a controlled fashion, such as at the patient's home. As such, a patient may also have to carry a bag or the like for collecting those accessories that have been exposed to blood.

In order to permit patients to provide their physician with medical data without having to visit the physician's office, systems have been developed that permit a patient to periodically log onto a computer in their home or office and to then uplink the medical data collected by the monitor to their physician for analysis. Upon analyzing the medical data, the physician can contact the patient if the medical data is abnormal or is approaching abnormal levels in order to ask the patient to either visit the physician at the physician's office for a more thorough examination or to prescribe some remedial action such as by adjusting the patient's medication, diet and pattern of rest and exercise such that the patient's condition will stabilize. While these systems free the patient from having to visit the physician's office as frequently, these systems still impose some delay between the time at which the medical data is collected and the time that the physician analyzes the medical data and suggests remedial action, if necessary. For example, in some of these systems, the monitor that is worn by the patient collects data at fairly regular intervals. The medical data may be uplinked to the physician, however, on a less frequent basis. As such, some delay is introduced between the time of collecting the data and the time of uplinking the medical data to the physician.

In order to further reduce any delays between the collection of the medical data by the patient and the provision of the medical data to a physician, systems have been developed to transmit the medical data collected by a patient to their physician without requiring the patient to log onto their computer and uplink the medical data to the physician. In this regard, systems have been developed that provide for the medical data to be transmitted from the patient to a computer or computer network that is accessible by the physician while the patient is engaged in their day-to-day activities. For example, the monitor can be configured to wirelessly transmit the medical data to a host computer for transmission to their physician on either a relatively continuous basis or on a periodic basis. In addition, the host computer can analyze the medical data and identify seemingly abnormal medical data. For example, in a system designed to permit a diabetic to transmit their blood sugar readings to their physician, the host computer can be configured to identify instances in which the blood sugar readings are either too high or too low and to provide an alert to the physician such that the physician can more quickly analyze the medical data and contact the patient with an appropriate remedy. In order to facilitate communications between a physician and the patient, some of these systems also provide a communications link from the physician to the patient such that the physician can transmit messages or actually verbally communicate with the patient in instances in which the physician wishes to prescribe appropriate remedial treatment.

While these systems are effective in uplinking medical data to a physician, a physician oftentimes would like to have additional data relating to activities of the patient since this additional data may assist in interpreting the medical data and formulating the proper treatment plan. With respect to a diabetic patient, for example, a physician is desirous not only of the blood sugar readings of the patient over a period of time, but also data relating to the time and content of the meals eaten by the patient, the time and duration of various physical activities undertaken by the patient and the time and duration of any periods of rest or sleep enjoyed by the patient. Based upon this additional data, the physician may determine if fluctuations in the blood sugar of the patient are attributable to the activities of the patient and, if so, may suggest modifications in the activities of the patient in order to ensure that the blood sugar of the patient remains within a desired range. In instances in which a patient physically visits a physician, the patient may describe their activities in order to assist the physician in analyzing the medical data. However, these descriptions are oftentimes incomplete and somewhat inaccurate as the patient may have difficulty remembering each activity to the level or detail desired by the physician.

As described by U.S. patent application Ser. No. 09/883,708 filed Jun. 19, 2001 by Louis G. Nemeth, et al., the contents of which are incorporated herein by reference in their entirety, systems have been developed for permitting medical data collected by ambulatory patients to be annotated with data defining various activities of the patients. In these systems, the medical data and the related data defining the activities of the patient may be transmitted to the physician without requiring the patient to visit the physician. While these systems advantageously provide the physician with a great wealth of information in addition to the medical data in order to assist in the interpretation of the medical data and to prescribe proper treatments for the medical condition, these systems generally require a computing device in addition to the medical monitoring device since the medical monitoring device is not generally configured to accept additional data relating to the activities of the patient. In this regard, the system may also include a portable computing device, such as a personal data assistant (PDA) or other personal information manager (PIM), a mobile telephone, a laptop computer or the like, which communicates with the medical monitoring device and which accepts input by the patient, such as input defining various activities of the patient. The portable computing device may also communicate with a computer system accessible by the physician in order to provide the physician with the medical data collected by the medical monitoring device as well as related data defining various activities of the patient. As such, a patient must not only carry the medical monitoring device and the related accessories, but also the computing device in order to provide detailed information relating to their various activities. As will be apparent, the addition of the computing device further complicates matters for the patient since the patient must carry the medical monitoring device and its related accessories as well as the computing device with them as they travel about during the day. In this regard, while carrying cases have been developed for storing a medical monitoring device and its related accessories, these carrying cases make no provision for a computing device and, as a result, the computing device must be carried separately.

In addition to medical data relating to the physiological and biological status of a patient, it would also be desirable to monitor other types of medical data including medical data that is not naturally occurring or preexisting within the patient. For example, it would be desirable to monitor and analyze medical data relating to biologically, medically or scientifically relevant drugs, proteins, hormones, molecules, chemicals, atoms, isotopes, compounds or other exogenous materials that are administered or applied to the patient. These materials may be administered or applied to the patient for a wide variety of purposes including the monitoring, diagnosing or treating of the patient, study or research including the study of normal physiology or behavior, the prevention of illness, the enhancement or embellishment of preexisting patient physiology or behavior or risk identification associated with patient physiology or behavior.

As a result of the wide variety of medical data that may be collected and analyzed, the third parties to whom the medical data is distributed may be equally varied and may desirably include pharmaceutical companies, biotechnology companies, research institutions, clinical trial organizations and the like, in addition to or instead of third parties who are responsible for the care of the patient. It would therefore be desirable to have a robust system and method for collecting and analyzing the wide variety of medical data and for selectively distributing information relating to the medical data to selected third parties for any of a variety of purposes.

Regardless of the type of medical data and the third party to whom information relating to the medical data will be distributed, it would be desirable to collect the medical data while the patient is ambulatory, or mobile. Furthermore, it would be desirable to provide an improved system for carrying a medical monitoring device and its related accessories, as well as any associated computing device in an organized and compact manner, while preventing contamination or soiling of the accessories. Moreover, it would be desirable to carry the medical monitoring device and any associated portable computing device in such a manner that the medical monitoring device and the portable computing device may communicate with one another, as well as with a remote computing device, such as the personal computer of the patient or a computer network, such as a computer network accessible by the patient's physician or other third party.

SUMMARY OF THE INVENTION

A portable storage case for housing a medical monitoring device is therefore provided that facilitates communications with the medical monitoring device, such as the downloading of data collected by the medical monitoring device, while the portable storage case is in transport. Advantageously, the portable storage case may store not only the medical monitoring device, but also the accessories required for the tests and a portable computing device for, among other things, receiving additional data relating to the various activities of the patient. As such, the portable storage case maintains the medical monitoring device, the portable computing device and all related accessories in a compact and organized manner while preventing soiling or other contamination of the accessories. In addition, a method for communicating with a medical monitoring device stored within a portable storage case is also provided according to the present invention.

According to one aspect of the present invention, a portable storage case is provided for housing a medical monitoring device, such as a blood glucose meter or the like. The portable storage case includes a case body defining an internal compartment. The case body is capable of being opened to access the internal compartment and those items therewithin. The portable storage case also includes a holder disposed within the internal compartment of the case body for receiving the medical monitoring device. The portable storage case may also include a number of subcompartments carried by the case body and disposed within the internal compartment for storing accessories associated with the medical monitoring device. In this regard, the portable storage case may include a disposable container, such as a disposable pouch, for collecting consumables following their use. The disposable container is preferably replaceable such that a container that has been at least partially filled with used consumables may be replaced with a new, empty container.

The portable storage case advantageously includes an integral data connector disposed within the internal compartment in a predetermined positional relationship with respect to the holder. As such, communication may be established between the integral data connector and a corresponding data connector carried by the medical monitoring device such that data collected by the medical monitoring device may be accessed, such as by being downloaded, once the medical monitoring device is received by the holder. The portable storage case may include various types of integral data connectors. In one embodiment, for example, the integral data connector is an integral electrical connector for establishing electrical communication with a corresponding data communications port of a medical monitoring device.

In addition to the case body and the medical monitoring device, the portable storage case of one aspect of the present invention also includes a portable computing device carried by the case body and capable of communicating with the medical monitoring device, such as via the integral data connector. In this regard, following use by the patient, data collected by the medical monitoring device may be downloaded to the portable computing device via the integral data connector of the portable storage case that engages the corresponding data connector of the medical monitoring device. The data may be downloaded to the portable computing device in accordance with a variety of different procedures, but, in one embodiment, the portable computing device includes a processing device for automatically detecting the availability of data and then triggering the medical monitoring device to download the data to the portable computing device. The portable computing device preferably includes a data entry mechanism, such as a keypad or the like, for permitting data relating to an activity of the patient to be entered. The portable computing device may also include a memory device for storing data downloaded from a medical monitoring device. In order to transmit the data collected by the medical monitoring device to a remote computing device, such as a server or the like on a computer network accessible by a physician, a parent or other third party, the portable storage case may include a modem for transmitting the data downloaded from the medical monitoring device. In this regard, the portable computing device may include the modem or, alternatively, the modem may be separate from the portable computing device.

The portable storage case is preferably configured to store the medical monitoring device, the portable computing device and all accessories in an organized and compact fashion and in a manner that reduces the risk of soiling or other contamination of the accessories. Moreover, the portable storage case is preferably configured to permit use of the portable computing device without exposing the medical monitoring device and the related accessories, thereby reducing the visibility of the medical monitoring device and the related accessories which may make the patient or others feel uncomfortable. As such, the portable storage case may include a divider for separating the internal compartment into first and second sections. In this regard, the holder and the medical monitoring device are disposed in the first section, along with the related accessories, while the portable computing device is disposed in the second section.

Thus, the portable computing device is physically and visibly separated from the medical monitoring device and the related accessories.

In use, the medical monitoring device is utilized to collect medical data from a patient, such as by analyzing a sample of blood and determining the blood sugar of the patient. Data collected by the medical monitoring device is then downloaded from the medical monitoring device stored within the portable storage case to the portable computing device carried by the portable storage case. In this regard, in embodiments in which the portable storage case includes an integral data connector in communication with the portable computing device, docking of the medical monitoring device within the storage case also establishes communication between the integral data connector and the corresponding data connector of the medical monitoring device to thereby permit data collected by the medical monitoring device to be downloaded to the portable computing device via the integral data connector. Moreover, data that has been collected by the medical monitoring device may be automatically detected by the portable computing device such that downloading of the data to the portable computing device is triggered if it is detected that data is available. Additional data may also be entered via the portable computing device to describe various activities of the patient in order to supplement the medical data collected by the medical device. Finally, the data downloaded from the medical monitoring device, as well as any additional data entered via the portable computing device, may be transmitted to a remote computing device and/or stored for later transmission or analysis.

Therefore, the portable storage case permits the medical monitoring device, related accessories and a portable computing device to be housed in a compact and inconspicuous manner while also facilitating downloading of the data collected by the medical monitoring device. In this regard, the data may be collected while the portable storage case is in transport and then transmitted to a remote computing device for analysis and, in some embodiments, to trigger alerts of various third parties, including physicians, parents and the like, if the medical data fall outside of predetermined bounds. As such, the portable storage case permits an ambulatory patient to readily carry all of the various devices and accessories required to collect the necessary medical data throughout the day while preventing the accessories from becoming soiled or otherwise contaminated. Moreover, the portable storage case and associated method permits medical data and any related data defining the activities of the patient to be transmitted while the patient remains on the move, such as to a physician, parent, caregiver or other third party, in order to reduce any delays between the time at which medical data is collected and any necessary treatment of the patient is administered.

BRIEF DESCRIPTION OF THE DRAWINGS

Figure 3:
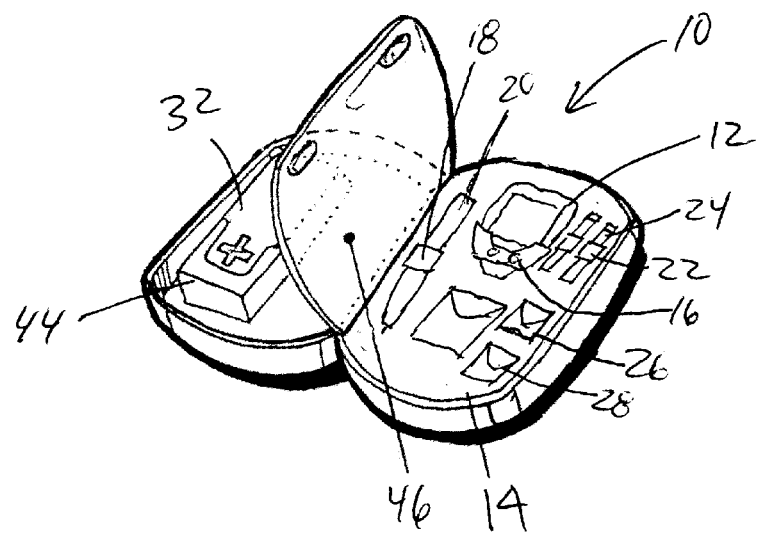
Figure 4:
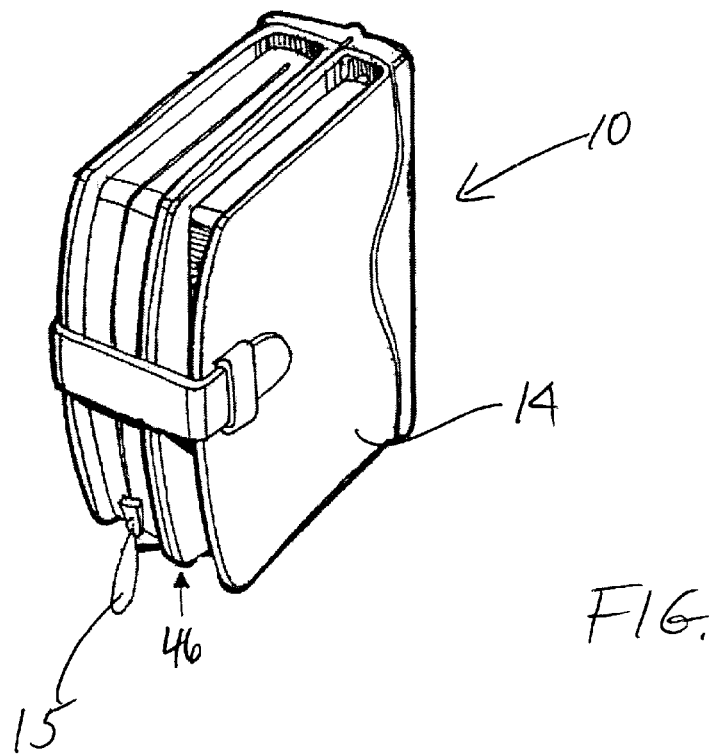
Figure 5:
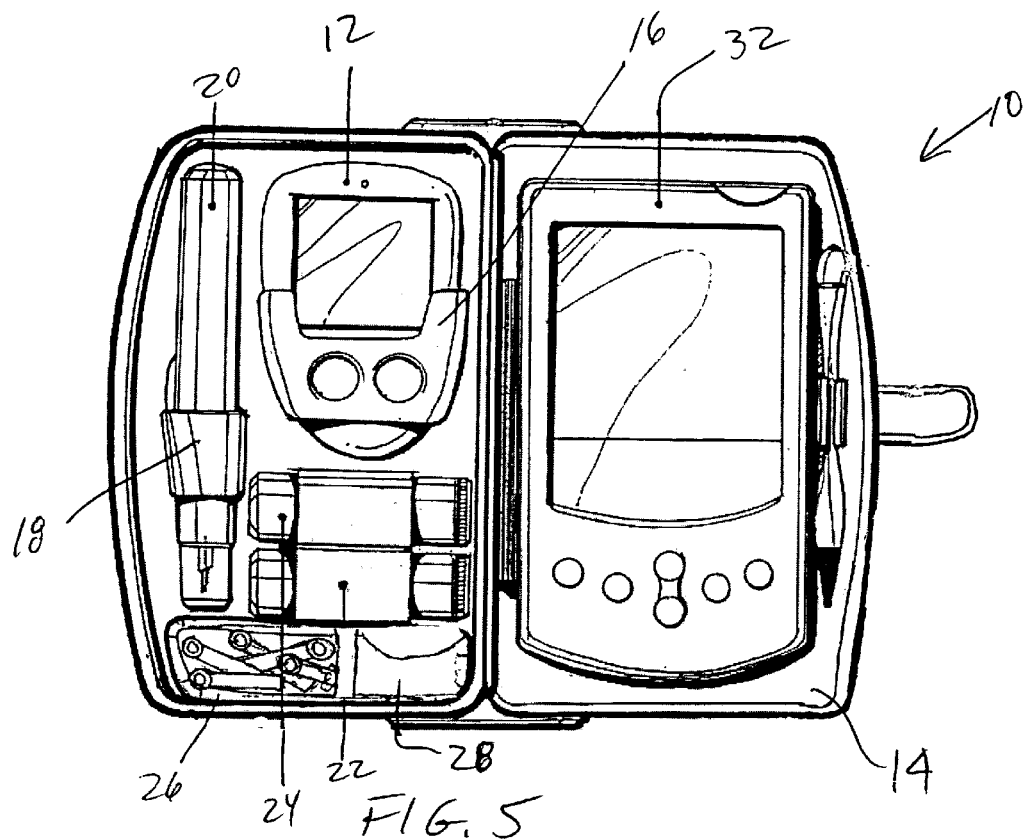
Figure 7:
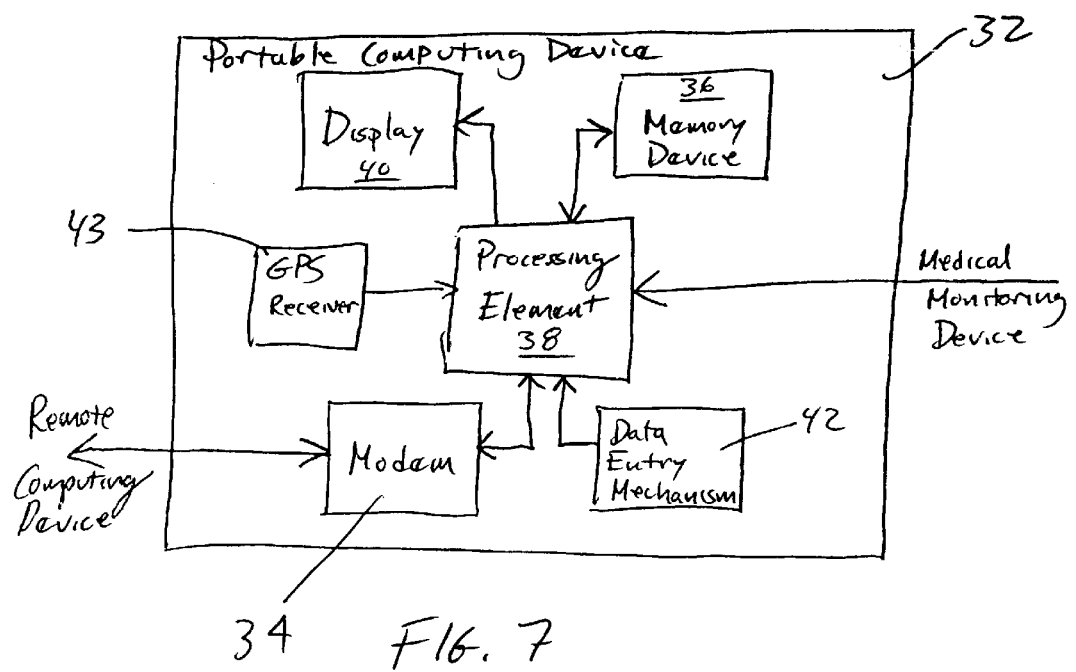
Figure 6:
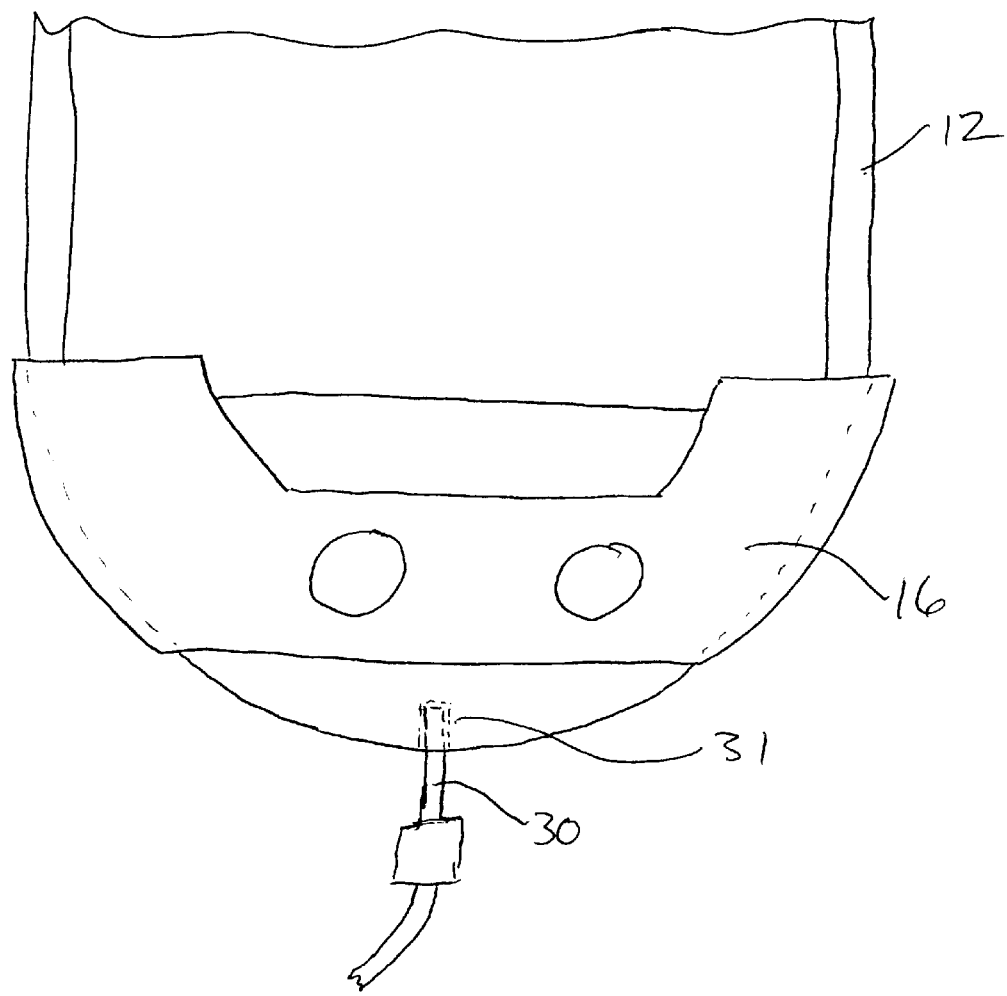
Figure 8:
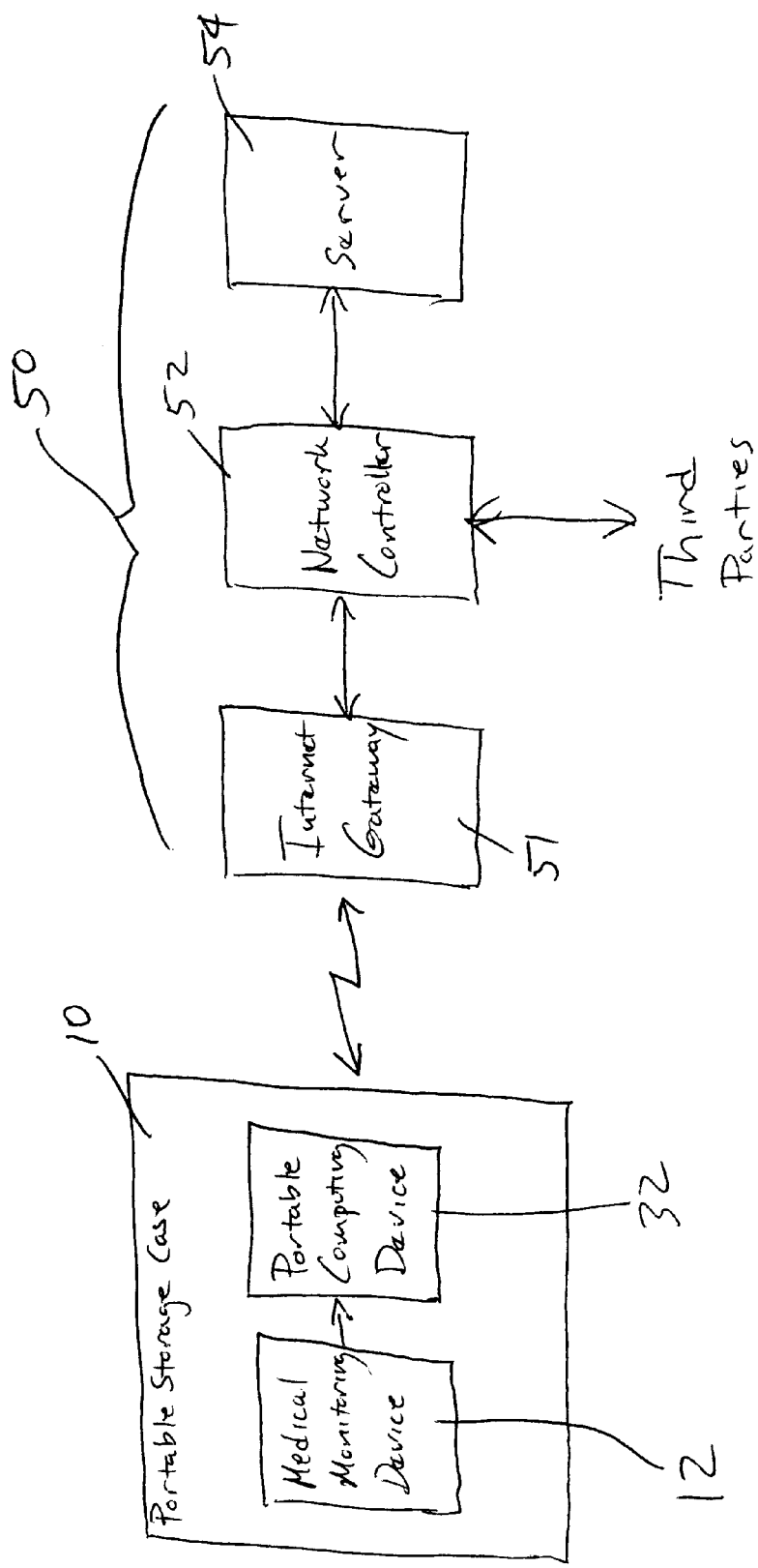
Figure 1:
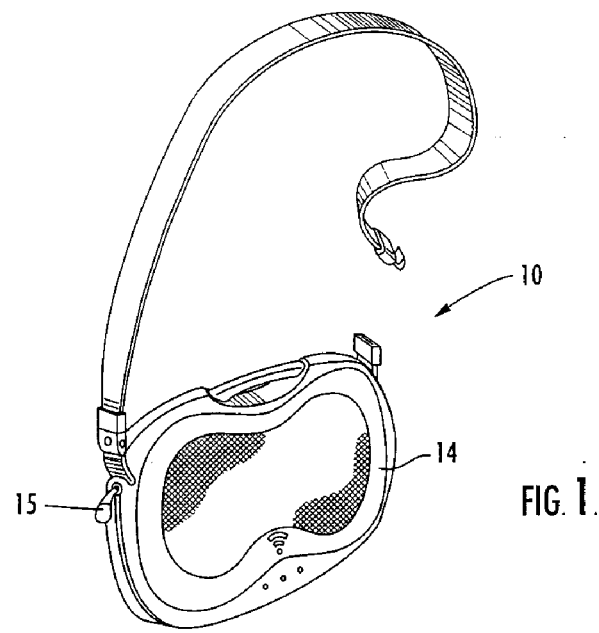
Figure 2:
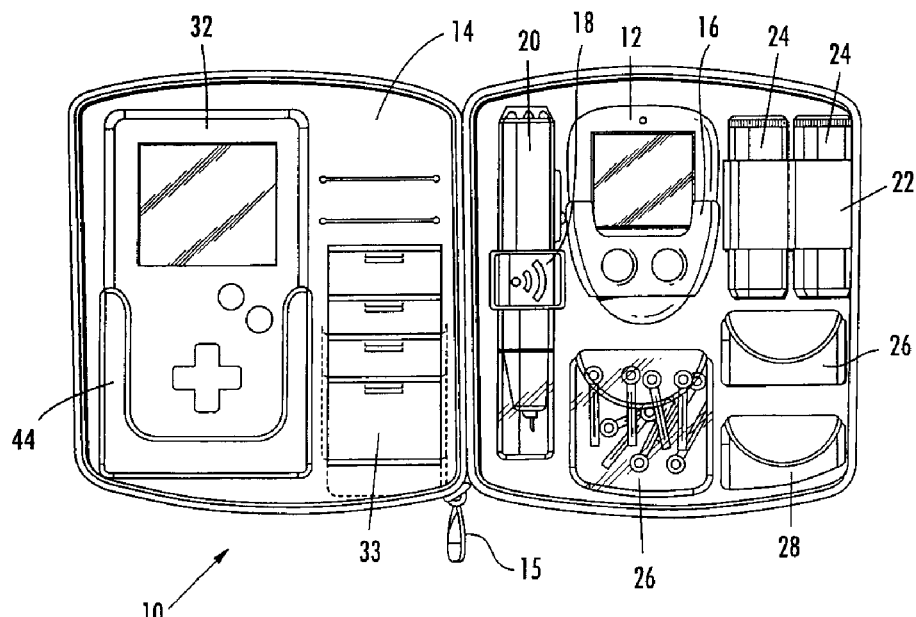
Figure 3:
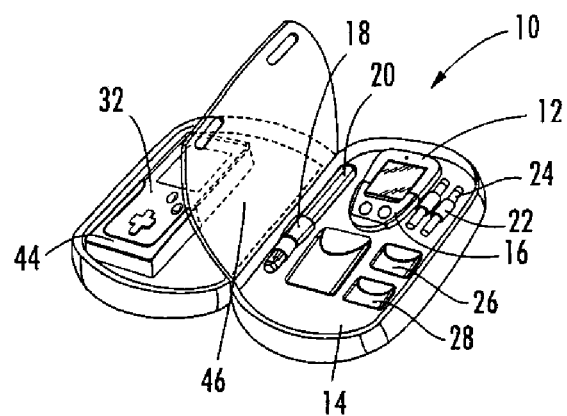
Figure 4:
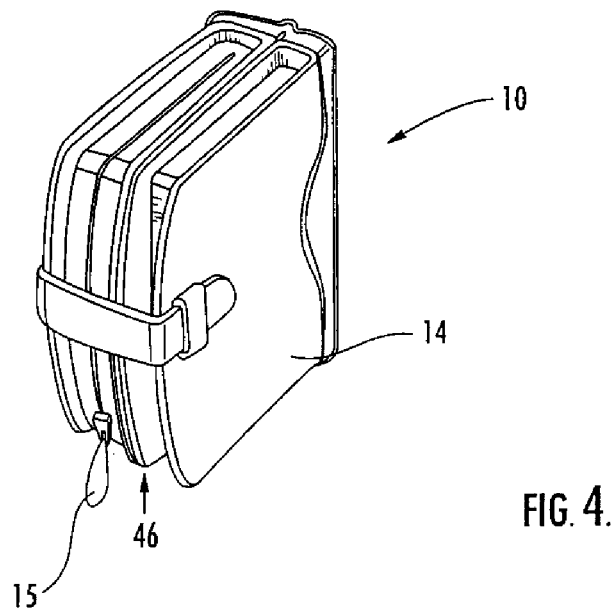
Figure 5:
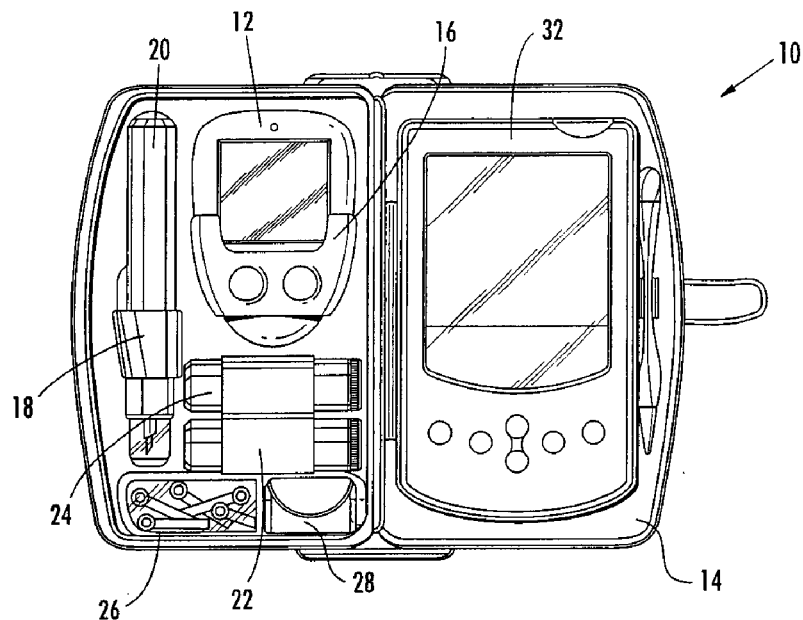
Figure 7:
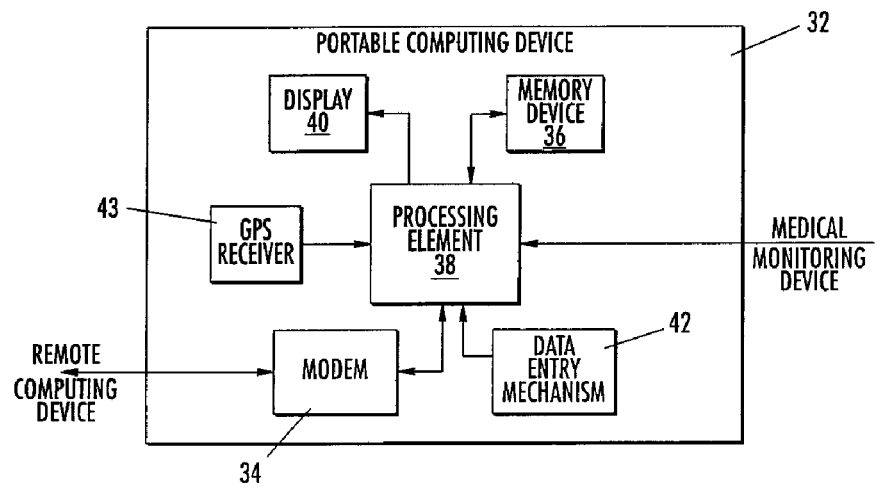
Figure 6:
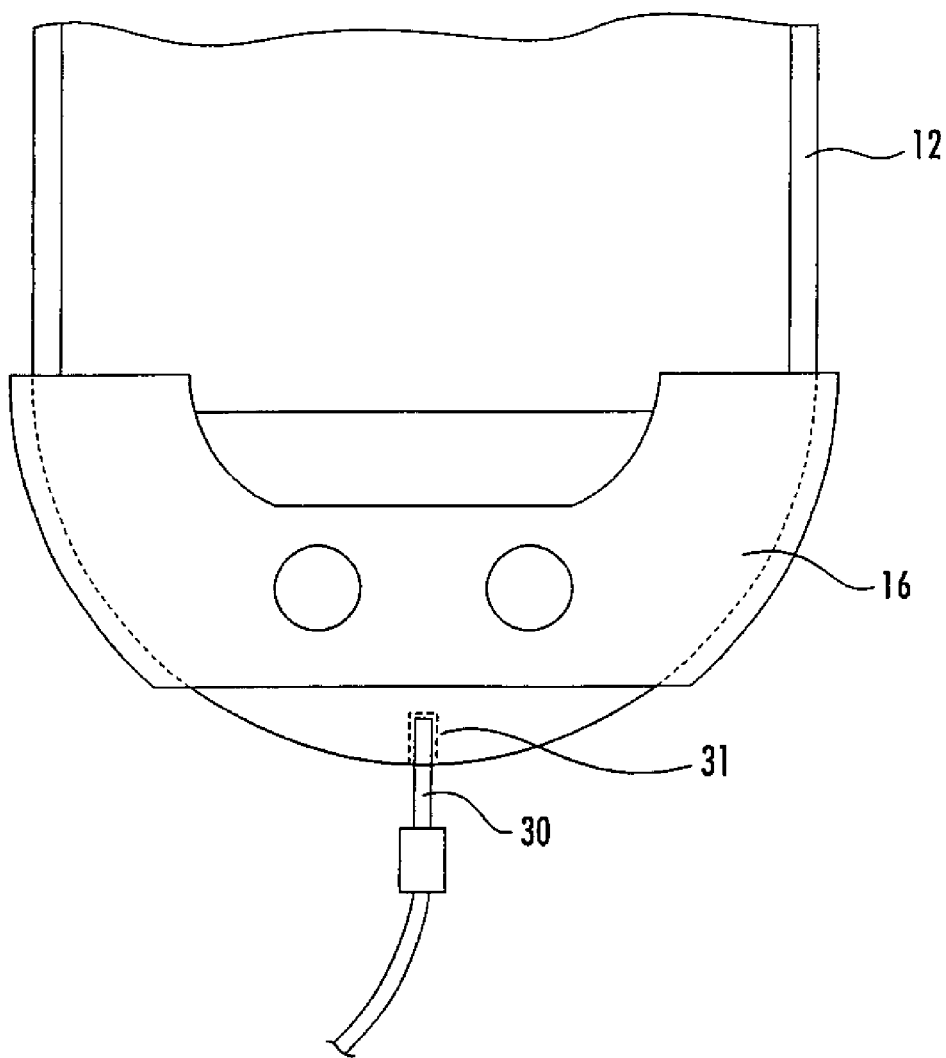
Figure 8:
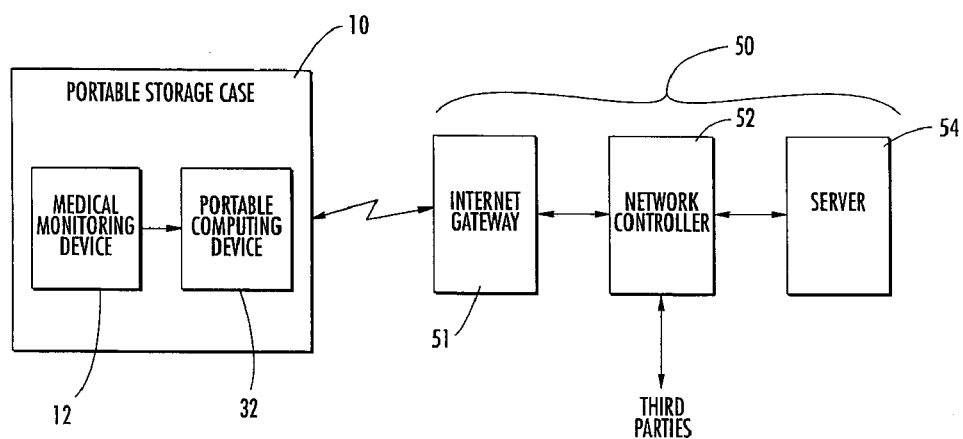

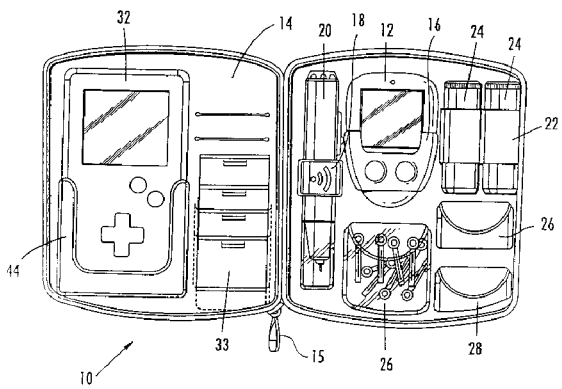

Having thus described the invention in general terms, reference will now be made to the accompanying drawings, which are not necessarily drawn to scale, and wherein:

FIG. 1 is a perspective view of a portable storage case in a closed configuration according to one embodiment of the present invention;

FIG. 2 is a plan view of the portable storage case of FIG. 1 in an open configuration and with the divider omitted for purposes of illustration;

FIG. 3 is a perspective view of the portable storage case of FIGS. 1 and 2 in the open configuration illustrating the separation of the internal compartment into first and second sections by a divider;

FIG. 4 is a perspective view of a portable storage case in a closed configuration according to another embodiment of the present invention;

FIG. 5 is a plan view of the portable storage case of FIG. 4 in an open configuration and with the divider omitted for purposes of illustration;

FIG. 6 is a fragmentary perspective view of an integral data connector of a portable storage case according to one embodiment of the present invention;

FIG. 7 is a block diagram of a portable computing device of a portable storage case of one embodiment of the present invention; and FIG. 8 is a schematic representation of a system for providing medical data from an ambulatory patient to a computer network by means of the portable storage case of one embodiment of the present invention.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Referring now to FIGS. 1–5, a portable storage case 10 for housing a medical monitoring instrument 12 is provided. While the portable storage case will be primarily described hereinafter in conjunction with a blood glucose meter, such as a One Touch® Ultra blood glucose monitoring system available commercially from Lifescan, Inc., for measuring the blood sugar of a diabetic patient, the portable storage case may house other types of medical monitoring devices, such as sensors, detectors, biomonitors and the like, that are utilized by ambulatory patients to collect a variety of different types of medical data. The medical data may relate to the physiological or biological status of a patient, such as a patient suffering from any of a number of medical conditions. For example, the patient can be suffering from a heart condition, such as an arrythmia or coronary artery disease, such that the medical data includes blood pressure, pulse rate, heart sounds, EKG and/or other heart-related parameters. Still further, a patient can be pregnant and the medical data can be the baby's heart rate, blood pressure and the like. By way of further example, the medical data may include the temperature, cholesterol or creatine kinase level of the patient, any data collected from a urinalysis of the patient and/or the HCG of a patient, such as for purposes of pregnancy determination. As such, medical data relating to the physiological or biological status of a patient includes all data relating to the physical condition and composition of the patient.

The medical data that is collected may also relate to a condition of the patient that is not preexisting or naturally occurring. For example, the medical data can include data relating to biologically, medically or scientifically relevant drugs, proteins, hormones, molecules, chemicals, atoms, isotopes, compounds or other exogenous materials administered or applied to the patient. These exogenous materials may be administered or applied to the patient for various purposes including, for example, the monitoring, diagnosis or treatment of the patient, study or research of a particular condition, prevention of an illness, enhancement or embellishment of preexisting patient physiology or behavior, study of normal physiology or behavior, or risk identification associated with physiology or behavior. For example, a drug, a protein or other exogenous material may be administered to a patient who has been determined to be susceptible to a particular condition or disease, such as breast cancer or osteoporosis, in order to maintain one or more parameters associated with the patient, such as a certain protein level, within a predefined therapeutic range so as to prevent or at least retard the onset of the condition or disease. Further details and examples of the various types of medical data that may be collected by a medical monitoring device as well as examples of different types of medical monitoring devices are provided by U.S. patent application Ser. No. 09/883,708, filed Jun. 18, 2001, by Louis G. Nemeth et al., the contents of which have been incorporated herein.

The medical monitoring device 12 is typically removed from the portable storage case 10 in order to obtain the reading. However, the medical monitoring device may be configured such that the medical monitoring device may remain within the storage case while still obtaining readings. In order to measure a patient's blood sugar, for example, a drop of blood may be placed on a test strip that is then inserted into a blood glucose meter while the blood glucose meter remains within the storage case.

In addition to collecting and temporarily storing the medical data, the medical monitoring device 12 preferably identifies the patient and the time and date at which each datum was collected, thereby time and date stamping each datum. Alternatively, the portable computing device 32 described hereinbelow may provide the time and date stamp. As used hereinafter, the term "medical data" shall include not only the data collected from the patient, but also any data identifying the patient and any time and date stamp applied to the data.

Regardless of the type of medical monitoring device 12, the portable storage case 10 includes a case body 14 defining an internal compartment and being capable of being opened to access the internal compartment. The case body may have various configurations and styles without departing from the spirit and scope of the present invention. For example, the case body may be in the form of a portfolio that is carried by the patient, a relatively small briefcase or the like that is carried by the patient either by means of handles, a shoulder strap or both, or a pack that may be strapped about the patient's waist or clipped to a belt.

In these configurations, the case body 14 includes a pair of opposed side walls and a mechanism for securing the side walls to one another in a closed position. As shown in FIGS. 1–3, for example, the side walls may be joined or hinged along one edge and a zipper 15 may extend along the other three edges to thereby permit the case body to alternately be opened and closed. Other mechanisms for securing the first and second side walls together may be utilized including, by way of further example, a flap that extends from one of the side walls and carries a snap or other type of clasp that may be engaged by a corresponding snap or clasp carried by the other side wall. See, for example, the embodiment of FIGS. 4 and 5. Regardless of the type of mechanism for securing the first and second side walls, the case body of the illustrated embodiment may be opened, such as by unzipping the zipper, to access the various items stored within the portable storage case 10 and may be closed, such as by zipping the zipper about the case body, in order to secure the items within the portable storage case during transport, storage or the like.

The case body 14 of one advantageous embodiment is capable of being fully opened such that the first and second side walls may lie flat upon a support surface, as shown in FIGS. 2 and 5. However, the case body may be constructed in other manners so long as an opening is provided to the internal compartment defined by the case body. For example, the first and second side walls may be joined along three sides, with an opening only provided along the one remaining side through which the contents of the portable storage case 10 could be accessed, much in the same manner as the contents of a handbag are accessed.

The case body 14 may be formed of various materials, but is preferably formed of a material sufficiently hard and durable to protect the items stored within the portable storage case 10 from damage during routine handling. In one example, the case body is formed of a plastic material that has been molded to have the desired shape. In order to improve the appearance of the case body, the plastic case body may be covered with a fabric or leather, if so desired. While the case body may be formed of plastic as described, the case body may be formed of other materials so long as the contents of the portable storage case are sufficiently protected from damage. The case body may also include one or more lights, such as one or more light emitting diodes, for providing an indication as to the functional and/or operational status of at least one of the electronic components stored therein, such as the medical monitoring device 12 and/or the portable computing device 32 described hereinbelow.

The portable storage case 10 includes a holder 16 disposed within the internal compartment of the case body 14 for receiving the medical monitoring instrument 12. As shown in FIGS. 2 and 5, the holder may be a cradle or the like for receiving and holding the medical monitoring device, such as a blood glucose meter. While the portable storage case may include various types of holders, the holder is preferably designed to securely receive the medical monitoring device such that the medical monitoring device does not unseat from the holder during normal transport and handling of the portable storage case. The holder is typically carried by the case body and, in particular, by one of the side walls of the case body.

To improve organization, the portable storage case 10 can include a number of subcompartments, such as pouches, sleeves or the like, for receiving and storing accessories used in conjunction with the medical monitoring device. Each of these subcompartments is also disposed within the internal compartment and is carried by the case body 14. As explained below, the subcompartments are preferably carried by the same side wall of the case body that carries the holder 16 such that the medical monitoring device 12 and the accessories are housed on the same side of the internal compartment. As shown in FIGS. 2 and 5, the portable storage case can include a variety of subcompartments depending upon the type of accessory to be stored. In the exemplary embodiment in which the medical monitoring device is a blood glucose meter, the accessories include a lancing device, lancets, test strips, calibration liquid and bandages. As such, a strap 18 may be provided for securing the lancing device 20 to a side wall of the case body and sleeves 22 may be provided for receiving tubes 24 containing the test strips and calibration liquid. In addition, pouches 26 may be provided for storing the lancets and the bandages. An additional container or pouch 28 may be provided for storing used supplies, such as bandages, lancets, test strips and the like, to thereby prevent unnecessary and undesirable exposure to accessories that have been exposed to blood. In this regard, the additional pouch for storing the contaminated consumables may be disposable such that the pouch may be replaced with a new, empty pouch, either on a periodic basis or once the pouch is full. In order to permit this pouch to be disposable, the pouch is preferably removably attached to the case body. For example, the case body may include an additional sleeve in which the disposable pouch is retained and serves, for example, as a liner, or the disposable pouch may be adhesively attached or attached by means of a hook and loop fastener or the like to the case body in such a manner that the disposable pouch may be separated from the case body and another disposable pouch may be attached. While one example of the subcompartments carried by the case body is described above and illustrated in FIGS. 2 and 5, the portable storage case can include a variety of other subcompartments, depending upon the type of accessories utilized in conjunction with the respective medical monitoring device.

According to one advantageous aspect of the present invention, the portable storage case 10 includes an integral data connector 30 disposed within the internal compartment in a predetermined positional relationship with respect to the holder 16. In this regard, the integral data connector is positioned such that communication is established between the integral data connector and a corresponding data connector 31 of the medical monitoring device 12 upon insertion of the medical monitoring device into the holder. In one embodiment depicted in FIG. 6, the integral data connector is an integral electrical connector, such as an integral electrical plug, secured to a side wall of the case body 14 for mating with and establishing electrical communication with a corresponding data communications port of the medical monitoring device. As such, the integral electrical connector is inserted into and mated with the corresponding data communications port of the medical monitoring device of this embodiment as the medical monitoring device is inserted into the holder. Thus, a patient need not take any additional actions in order to establish communication with the medical monitoring device other than merely inserting the medical monitoring device into the holder since the position of the integral data connector is designed such that the insertion of the medical monitoring device into the holder establishes communication between the integral data connector and a corresponding data connector carried by the medical monitoring device.

Once communication is established between the integral data connector 30 and a corresponding data connector 31 carried by the medical monitoring device 12, data that has been collected by the medical monitoring device may be accessed. In this regard, the medical monitoring device and/or the portable computing device 32 described below may be connected to a modem that is external to the portable storage case 10, such as by means of an electrical connector or the like. The modem, in turn, may transmit the data downloaded from the medical monitoring device and/or the portable computing device to a remote computing device.

Alternatively, the portable storage case 10 may include an internal modem connected to the integral data connector 30, such as by means of electrical wiring, an infrared or radio frequency (RF) data link or the like, for receiving the data collected by the medical monitoring device 12 and then transmitting the data to a remote computing device, such as the personal computer of the patient or a third party or a network server 54 as described below. In one advantageous embodiment, the portable storage case also includes a portable computing device 32 that is carried by the case body 14 and is capable of communicating with the medical monitoring device while the medical monitoring device is disposed within the internal compartment. In particular, the portable computing device may be communicably connected to the integral data connector in order to receive the data that has been collected by the medical monitoring device once the medical monitoring device has been docked or stored within the holder 16 and communication has been established between the integral data connector and the corresponding data connector 31 carried by the medical monitoring device. As shown schematically in FIG. 7, the portable computing device generally includes the modem 34 for transmitting data downloaded from the medical monitoring device to a remote computing device as described hereinbelow.

Additionally, the portable computing device 32 may include a memory device 36 for storing data downloaded from the medical monitoring device 12. In this regard, if the communication channel to the remote computing device is unavailable, such as in instances in which the portable computing device is temporarily out of range, or if the portable computing device is otherwise not yet prepared to transmit the data downloaded from the medical monitoring device to the remote computing device, the data downloaded from the medical monitoring device may be stored within the memory device of the portable computing device.

The data may be downloaded from the medical monitoring device 12 to the portable computing device 32 in any of a variety of manners. For example, in instances in which the medical monitoring device is removed from the case body 14 in order to obtain a reading, the medical monitoring device may automatically download all of the data collected since the last time that the data has been downloaded upon the return of the medical monitoring device to the holder 16 and the establishment of communication between the integral data connector 30 and the corresponding data connector 31 carried by the medical monitoring device. Alternatively, the portable computing device may include a processing element 38 for detecting the establishment of communication between the integral data connector and the corresponding data connector carried by the medical monitoring device, such as upon the return of the medical monitoring device to the holder. The processing element of the portable computing device may then poll the medical monitoring device to determine if additional data has been collected and is available for downloading. If so, the processing element of the portable computing device can issue a signal triggering the downloading of the data from the medical monitoring device. In order to accommodate instances in which the medical monitoring device is not removed from the case body in order to obtain a reading, the medical monitoring device may be configured to attempt to download data that has been collected immediately following the collection of the data and/or the portable computing device may be configured to repeatedly poll the medical monitoring device for any additional data that has been collected.

While the portable computing device 32 can store the downloaded data and/or re-transmit the data to a remote computing device in the same form as provided by the medical monitoring device 12, the portable computing device and, in particular, the processing element 38 of the portable computing device may perform various predetermined analyses upon the data and may provide the results of those analyses along with the underlying data to the remote computing device, if so desired. Additionally, the portable computing device may include a display 40 driven by the processing element for displaying the data and, in some embodiments, the results of various analyses of the data. For example, the display may graphically depict the data collected at various points in time, either in terms of the raw data that was collected by the medical monitoring device or in terms of averages. Additionally, any instances in which the data fell outside of predetermined bounds may be graphically identified.

The portable computing device 32 may also include a data entry mechanism 42 for permitting data relating to an activity of the patient to be entered. Typically, the data entry mechanism is a keypad. However, other data entry mechanisms may be utilized, including a touch screen display or by means of selections presented by a menu-driven software program or the like that has been configured or customized by the patient. While the data that is input by the patient will vary depending upon the medical data being collected, the data that is input by a diabetic patient generally relates to the patient's medication, insulin administration, diet and/or the amount of rest and exercise that the patient has had. In addition, the data that is input by the patient may relate to stress, i.e., the occurrence of an unusually stressful situation, the illness of the patient, or a particular activity that the patient undertook. For example, a diabetic patient can enter data relating to their caloric intake, medication that has been taken, the length of any rest periods and the types of exercise performed by the patient as well as the respective times of these events. The additional data entered via the data entry mechanism may be stored by the memory device 36, analyzed by the processing element 38 and/or transmitted to the remote computing device in the same manner as the data downloaded from the medical monitoring device 12. The data input by the patient can then be factored into the analysis performed by the third party in order to properly interpret the medical data.

The portable computing device 32, or in some embodiments the medical monitoring device 12, may also include means for determining the location of the patient. For example, the portable computing device may include a global positioning system (GPS) receiver 43 for determining the coordinate position of the ambulatory patient. While the portable computing device may include a GPS receiver as depicted in FIG. 7, the medical monitoring device can include the GPS receiver, in which instance the monitor will provide signals indicative of the position of the patient to the portable computing device. Alternatively, other means may be provided for determining the location of the patient may be provided as described by U.S. patent application No. 09/883,708.

While the portable computing device 32 can be embodied in many different devices, the portable computing device is oftentimes a device that is utilized by the patient for other purposes, but that can support the functionality required by the present invention. In this regard, the portable computing device can be a mobile telephone, a pager (preferably a two-way pager), a personal digital assistant (PDA) or other personal information manager (PIM), a notebook computer, a handheld computer, a handheld video game terminal, such as a GAMEBOY® terminal, or the like. By way of example, the portable storage case 10 of the embodiment depicted in FIGS. 1–3 includes a handheld video game terminal, such as a GAMEBOY® terminal, as the portable computing device. As such, the portable storage case of the embodiment of FIGS. 1–3 is particularly well suited for juvenile patients who are accustomed to operating handheld video game terminals. As a further example, the portable storage case of the embodiment of FIGS. 4 and 5 includes a PDA and an associated stylus as the portable computing device. However, other types of portable computing devices can be employed without departing from the spirit and scope of the present invention.

By way of example, the medical monitoring device 12 may be a blood glucose meter, such as a One Touch® Ultra blood glucose monitoring system available commercially from Lifescan, Inc., and the portable computing device 32 may be a Timeport™ P935 personal communicator that is available commercially from Motorola, Inc. The portable storage case 10 of this exemplary embodiment may also include an integral electrical connector 30 for engaging a corresponding data communications port 31 of the blood glucose meter. Since the Timeport™ P935 personal communicator is designed to communicate via infrared transmission, the portable storage case may also include a communications module including an infrared transceiver to convert between electrical signals and infrared signals. Thus, electrical signals transmitted from the blood glucose meter will be converted to infrared signals prior to presentation to the Timeport™ P935 personal communicator, while infrared signals transmitted from the Timeport™ P935 personal communicator will be converted to electrical signals prior to presentation to the blood glucose meter. It should be understood, however, that the medical monitoring device and the portable computing device may communicate in other manners without departing from the spirit and scope of the present invention. For example, electrical wiring can directly connect the integral data connector and the portable computing device. Alternatively, a wireless transceiver or modem may be connected to the integral data connector to facilitate wireless communications between the portable computing device and the medical monitoring device.

The portable computing device 32 is also typically carried by the case body 14, as shown in FIGS. 2 and 5. In this regard, the portable storage case may include another holder 44 for retaining the portable computing device. While the portable computing device may be carried in a pocket or the like on the outside of the case body in order to permit ready access to the portable computing device, the portable computing device is more commonly carried within the internal compartment defined by the case body and is secured to the side wall opposite from the side wall that carries the medical monitoring device 12. In this embodiment, the portable storage case may also include a divider 46 disposed within the internal compartment and connected along one edge to the case body. As shown in FIG. 3, the divider preferably extends from the edge that joins the first and second side walls of the case body so as to separate the internal compartment into first and second sections. The first section of the internal compartment includes those components carried by the first side wall of the case body, such as the medical monitoring device and the related accessories. In addition, the second section includes those items carried by the second side wall of the case body, such as the portable computing device, memory cartridges 33 and the like. As such, the portable computing device may be separated, both visually and physically, from the medical monitoring device and related accessories. This separation may be advantageous in instances, for example, in which the portable storage case has a portfolio or similar design so as to enable the patient to open the portfolio and utilize the portable computing device in a business setting without exposing the medical monitoring device and related accessories since the medical monitoring device and related accessories may make either the patient or others somewhat uneasy. While the divider is described hereinabove to cover the medical monitoring device and the related accessories, the divider is preferably connected to the case body such that the divider may be moved so as to cover either the portable computing device or the medical monitoring device and related accessories, depending upon the components to be utilized by the patient.

The medical data received by the portable computing device 32 is generally transmitted to a remote computing device. The medical data may be transmitted to various types of remote computing devices. For example, the portable computing device may transmit the medical data to the personal computer of the patient or a third party. As described below in conjunction with communication between the portable computing device and a computer network 50, the portable computing device may communicate with a personal computer in a variety of manners including communicating wirelessly via a radio frequency or infrared link, typically while the portable computing device remains within the case body 14. By way of further example, the portable computing device may be hot-synced with a personal computer, also typically while the portable computing device remains within the case body as a result of a connector extending from the portable computing device that that is accessible on the exterior of the portable storage case 10.

Typically, however, the portable computing device 32 transmits the medical data to a computer network 50 for distribution to the third party, as shown schematically in FIG. 8. The portable computing device may transmit the data via a hardwire connection. However, the portable computing device typically transmits the data wirelessly, such as via a wide-area wireless network such as a paging network, a satellite network or a mobile telephone data network. In particular, the portable computing device typically transmits the medical data via radio frequency communications or other wireless means to an internet gateway 51 that receives the medical data and provides the medical data to the computer network. As shown in FIG. 8, the computer network typically includes a network controller 52 and an associated server 54, memory device or the like for storing the medical data in a secure fashion for retrieval by the third party. In addition to transmitting the medical data, the portable computing device preferably also transmits any information relating to the position of the patient as well as data input by the patient, such as data related to the patient's diet, rest, exercise, medication, stress, illness or activity. This information is also generally stored by the server along with the medical data from the patient, and is also accessible by the third party. In order to protect the confidentiality of the medical data, the portable computing device and, more particularly, the processing element 38 may encrypt the medical data prior to transmission to the computer network.

The portable computing device 32 preferably relays the medical data and all related information to the computer network 50 immediately upon receipt by the portable computing device from the medical monitoring device 12 borne by the ambulatory patient. However, the portable computing device may temporarily store the medical data and related information in the memory device 36 for some period of time. For example, in instances in which the portable computing device is out of range of the computer 10 network, the portable computing device may store the medical data and related information until it again becomes in range and can transmit the medical data and related information to the computer network. Alternatively, the portable computing device may temporarily store the medical data and related information such that the medical data and other related information can be intermittently transmitted to the computer network. Examples of transmission schemes for intermittently transmitting the medical data and related information to a computer network are provided by U.S. patent application Ser. No. 09/883,708.

By way of example in conjunction with the embodiment of the present invention in which the portable computing device 32 is a Timeport™P935 personal communicator, the medical data and related information may be wirelessly transmitted via the ReFLEX two-way paging network to the computer network 50 for review by a third party. Since the protocol or format of the signals transmitted by the portable computing device, such as a Timeport™ P935 personal communicator, may differ from the protocol or format of the signals processed by the computer network, the computer network may include a module for translating between the different protocols or formats.

Once the medical data and related information are received by the computer network 50, the medical data and related information may be accessed by the third party who has been identified by the patient, such as by means of a configurable notification record as described in detail by U.S. patent application Ser. No. 09/596,325 filed Jun. 19, 2000 by Louis G. Nemeth, et al., the contents of which are incorporated in their entirety herein, as well as U.S. patent application Ser. No. 09/883,708. While the third party can access the medical data and other related information stored on the server 54 for the particular patient from whom the third party has permission, the third party cannot access the medical data or other information stored on the server for other patients, thereby protecting the integrity and confidentiality of the medical data and other information. As such, the computer system 50 serves as a virtual private network for the patient and the third party. Based upon an analysis of the medical data and other related information, the third party can direct the patient to take remedial action in order to correct an abnormal condition or to otherwise insure that the patient remains in a relatively normal condition.

While advantageous for providing medical data as well as appropriate alerts and warnings to a third party who is responsible for the care of the patient, such as parents, guardians, nurses, health care professionals, physicians and the like, the medical data and any related information including any associated alerts and warnings may instead be provided to a wide variety of other third parties depending upon the application of the system and method of the present invention. For example, the third parties may include pharmaceutical companies, biotechnology companies, research institutions, clinical trial organizations and the like who collect medical data regarding a patient population for a variety of purposes depending upon the mission of the third party. In order to preserve the confidentiality of the patients, the medical data will commonly be deidentified aggregate data of a population of patients. As such, the term "medical data" will also include the deidentified aggregate data of a population of patients for purposes of this patent application.

In addition to merely providing the medical data and other related information for review by the third party, the computer network 50 and, in particular, the network controller 52 may analyze the medical data and provide the third party with an alert if the medical data meets the established conditions for an alert as also described in more detail in U.S. patent application Ser. Nos. 09/596,325 and 09/883,708. While the conditions that trigger an alert will depend upon the type of medical data that is being collected, alerts are typically triggered if the readings are outside of a predetermined range by being either too large or too small or if the rate of change of the readings exceed a predetermined threshold. However, a wide variety of other types of alerts are certainly possible and within the spirit and scope of the present invention. Upon receipt of an alert, the third party will typically review the medical data and other related information in a prompt manner and will provide instructions to the patient for any necessary remedial action.

In this regard, the communications link between the portable computing device 32 and the computer network 50 also supports communications from the third party to the patient so that the third party may instruct the patient to take certain remedial measures. In one embodiment in which the blood sugar of an ambulatory patient is being monitored, a third party can provide instructions regarding the administration of insulin to the patient in instances in which the patient's blood sugar has dropped precariously low. These instructions may be displayed upon the display 40 of the portable computing device and an alarm may be provided to the patient, if desired.

The communications link between the portable computing device 32 and the computer network 50 also supports a wide variety of other communications from the computer network to the portable computing device. For example, a care plan may be established for a patient that defines a schedule of events designed to permit the patient's condition to be properly monitored and/or controlled. In this regard, a care plan may define a number of specific times throughout each day at which an ambulatory patient is to obtain a reading, such as a reading of their blood sugar for a diabetic patient, eat a meal, exercise, rest or the like. In the event that the computer network is not notified of the occurrence of the event within a predetermined window of time surrounding the time at which the event was scheduled to occur, the computer network may transmit an inquiry, i.e., a non-compliance alert, to the portable computing device asking the patient to perform the scheduled event and to transmit the medical data relating to the event to the computer network. As will be apparent, the parameters defining the non-compliance alert may be configurable, such as by the patient and/or by the third party, during or following the construction of the care plan for the patient. In order to further prompt a patient to respond to a non-compliance alert or any other inquiry from the computer network, the portable storage case 10 may also include a speaker, a vibrator or other means for notifying the patient that an inquiry has been received and may displayed upon the display 40 of the portable computing device. In one embodiment, the speaker, vibrator or other notification means is designed to notify a patient even in instances in which the case body 14 is closed, such as by producing an audible alert that may be heard while the case body is closed. With respect to an audible alert, the portable storage case may include an acoustically transparent window that overlies the speaker with the window being covered by a material that is much thinner than the acoustic wavelength in the material at the highest frequency of interest. It should be understood, however, that other means of acoustically coupling or amplifying the audible alert produced by the speaker through the case body may be employed.

As described above, a patient can enter additional data into the portable computing device 32, typically via the data entry mechanism 42, relating to their activities, such as data relating to meals, exercise, rest, medication and the like. In order to simplify the process of entering this additional data, the portable computing device may provide one or more menus of predefined types of activities. The patient can then select the predefined type of activity from the menu and can enter any additional parameters solicited by the portable computing device in conjunction with the selected activity, such as the caloric content of a meal, the type and duration of exercise, the duration of a rest period or the quantity of medication. In addition to the establishment of a care plan, the menus of predetermined types of activities may be constructed by the patient and/or a third party during the initial configuration and/or a subsequent reconfiguration of the portable computing device. The resulting menu structure as well as any other configuration information may subsequently be transmitted from the computer network 50 to the portable computing device.

Other types of communications may be directed from the computer network 50, such as from a third party, to the portable computing device 32. For example, inquiries may be transmitted to the patient to obtain subjective data including the answers to questions such as "how are you feeling?" and "did you gain weight?". Additionally, the computer network may monitor the operational status of and to perform some diagnostics upon the portable computing device, the medical monitoring device 12 or other electronic components carried by the portable storage case 10, such as by checking the battery life remaining.

As described above, the portable storage case 10 permits the medical monitoring device 12, related accessories and a portable computing device 32 to be housed in a compact and inconspicuous manner while also facilitating downloading of the data collected by the medical monitoring device. In this regard, the data may be collected while the portable storage case is in transport and then transmitted to a remote computing device for analysis and, in some embodiments, to trigger alerts of various third parties, including physicians, parents and the like, if the medical data fall outside of predetermined bounds. As such, the portable storage case permits an ambulatory patient to readily carry all of the various devices and accessories required to collect the necessary medical data throughout the day while preventing the accessories from becoming soiled or otherwise contaminated. Moreover, the portable storage case and associated method permits medical data and any related data defining the activities of the patient to be transmitted while the patient remains on the move, such as to a physician, parent, caregiver or other third party, in order to reduce any delays between the time at which medical data is collected and any necessary treatment of the patient is administered.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A portable storage case for housing a medical monitoring device comprising:

a case body defining an internal compartment, said case body capable of being opened to access the internal compartment;

a holder disposed within the internal compartment of said case body for receiving the medical monitoring device; and an integral data connector disposed within the internal compartment in a predetermined positional relationship with respect to said holder such that communication is established between said integral data connector and a corresponding data connector carried by the medical monitoring device to thereby permit data collected by the medical monitoring device to be accessed once the medical monitoring device is received by the holder.

2. A portable storage case according to claim 1 wherein said integral data connector comprises an integral electrical connector for establishing electrical communication with a corresponding data communications port of the medical monitoring device.

3. A portable storage case according to claim 1 further comprising a portable computing device carried by said case body and capable of communicating with the medical monitoring device via said integral data connector.

4. A portable storage case according to claim 3 wherein said portable computing device comprises a data entry mechanism for permitting data relating to an activity of a patient to be entered.

5. A portable storage case according to claim 3 further comprising a divider for separating the internal compartment into first and second sections, wherein said holder is disposed in the first section and said portable computing device is disposed in the second section such that said portable computing device is separated from the medical monitoring device.

6. A portable storage case according to claim 3 wherein said portable computing device comprises a processing element for automatically detecting availability of data from the medical monitoring device in order to trigger downloading of the data to said portable computing device.

7. A portable storage case according to claim 3 wherein said portable computing device comprises a memory device for storing data downloaded from the medical monitoring device.

8. A portable storage case according to claim 1 further comprising a modem for transmitting data downloaded from the medical monitoring device to a remote computing device.

9. A portable storage case according to claim 1 wherein the medical monitoring device is a blood glucose meter.

10. A portable storage case according to claim 1 further comprising a plurality of subcompartments carried by said case body and disposed within the internal compartment for storing accessories associated with the medical monitoring device.

11. A portable storage case according to claim 10 wherein at least one of said subcompartments is comprised of a disposable and replaceable container for receiving accessories consumed during collection of the medical data.

12. A portable storage case according to claim 1 wherein said portable computing device comprises a handheld video game terminal.

13. A portable storage case for housing a medical monitoring device comprising:
 a case body defining an internal compartment, said case body capable of being opened to access the internal compartment;
 a medical monitoring device disposed within the internal compartment and carried by said case body; and
 a portable computing device carried by said case body and capable of communicating with said medical monitoring device while said medical monitoring device is disposed within the internal compartment to thereby permit data collected by said medical monitoring device to be transferred to said portable computing device.

14. A portable storage case according to claim 13 wherein said portable computing device comprises a data entry mechanism for permitting data relating to an activity of a patient to be entered.

15. A portable storage case according to claim 13 further comprising a divider for separating the internal compartment into first and second sections, wherein said medical monitoring device is disposed in the first section and said portable computing device is disposed in the second section such that said portable computing device is separated from said medical monitoring device.

16. A portable storage case according to claim 13 wherein said portable computing device comprises a processing element for automatically detecting availability of data from said medical monitoring device in order to trigger downloading of the data to said portable computing device.

17. A portable storage case according to claim 13 wherein said portable computing device comprises a memory device for storing data downloaded from said medical monitoring device.

18. A portable storage case according to claim 13 further comprising a modem for transmitting data downloaded from said medical monitoring device to a remote computing device.

19. A portable storage case according to claim 13 wherein said medical monitoring device is a blood glucose meter.

20. A portable storage case according to claim 13 further comprising a plurality of subcompartments carried by said case body and disposed within the internal compartment for storing accessories associated with said medical monitoring device.

21. A portable storage case according to claim 20 wherein at least one of said subcompartments is comprised of a disposable and replaceable container for receiving accessories consumed during collection of the medical data.

22. A portable storage case according to claim 13 further comprising an integral data connector disposed within the internal compartment and in communication with said portable computing device, said integral data connector disposed in a predetermined positional relationship with respect to said medical monitoring device such that communication is also established between said integral data connector and a corresponding data connector of said medical monitoring device to thereby permit data collected by said medical monitoring device to be downloaded to said portable computing device once said medical monitoring device is disposed within the internal compartment.

23. A portable storage case according to claim 22 wherein said integral data connector comprises an integral electrical connector for establishing electrical communication with a corresponding data communications port of said medical monitoring device.

24. A portable storage case according to claim 13 wherein said portable computing device comprises a handheld video game terminal.

25. A method of establishing communication with a medical monitoring device during storage thereof, the method comprising:
 providing a portable storage case including a portable computing device;
 storing the medical monitoring device within the portable storage case; and
 downloading data collected by the medical monitoring device to the portable computing device while the medical monitoring device is stored within the portable storage case, wherein the portable storage case is capable of being transported while the data is downloaded.

26. A method according to claim 25 further comprising entering data relating to an activity of a patient to be entered via the portable computing device.

27. A method according to claim 25 further comprising:
- automatically detecting if data is available from the medical monitoring device once the medical monitoring device is docked within the portable storage case; and
- triggering the downloading of the data to the portable computing device if available data is detected.

28. A method according to claim 25 further comprising transmitting data downloaded from the medical monitoring device to a remote computing device.

29. A method according to claim 25 further comprising storing data downloaded from the medical monitoring device.

30. A method according to claim 25 wherein providing the portable storage case comprises providing the portable storage case having an integral data connector in communication with the portable computing device, and wherein docking the medical monitoring device comprises also establishing communication between the integral data connector and a corresponding data connector of the medical monitoring device to thereby permit data collected by the medical monitoring device to be downloaded to the portable computing device via the integral data connector.

31. A method according to claim 25 further comprising storing accessories associated with the medical monitoring device within a plurality of subcompartments of the portable storage case.

* * * * *

UNITED STATES PATENT AND TRADEMARK OFFICE
CERTIFICATE OF CORRECTION

PATENT NO. : 6,781,522 B2
DATED : August 24, 2004
INVENTOR(S) : Sleva et al.

It is certified that error appears in the above-identified patent and that said Letters Patent is hereby corrected as shown below:

The title page should be deleted to appear as attached title page.

The sheets of drawings consisting of figures 1-8 should be deleted to appear as per attached figures 1-8.

Signed and Sealed this

Sixteenth Day of November, 2004

JON W. DUDAS
*Director of the United States Patent and Trademark Office*

(12) United States Patent
Sleva et al.

(10) Patent No.: US 6,781,522 B2
(45) Date of Patent: Aug. 24, 2004

(54) PORTABLE STORAGE CASE FOR HOUSING A MEDICAL MONITORING DEVICE AND AN ASSOCIATED METHOD FOR COMMUNICATING THEREWITH

(75) Inventors: Michael Zigmund Sleva, Charlotte, NC (US); Kevin James Schimelfenig, Huntersville, NC (US); Kyle McGeever Schimelfenig, Huntersville, NC (US)

(73) Assignee: Kivalo, Inc., Huntersville, NC (US)

( * ) Notice: Subject to any disclaimer, the term of this patent is extended or adjusted under 35 U.S.C. 154(b) by 518 days.

(21) Appl. No.: 09/935,311

(22) Filed: Aug. 22, 2001

(65) Prior Publication Data

US 2003/0038047 A1 Feb. 27, 2003

(51) Int. Cl.[7] ............................................... G08C 17/00
(52) U.S. Cl. .................. 340/870.1; 361/683; 361/724; 361/728; 600/372; 706/569; 706/570
(58) Field of Search ....................... 340/870.1; 361/683, 361/685, 724, 728; 206/570, 569, 718; 600/504, 372

(56) References Cited

U.S. PATENT DOCUMENTS

| 3,786,510 A | 1/1974 | Hodges |
| 4,429,793 A | 2/1984 | Ehmann |
| 4,770,328 A | 9/1988 | Dickhudt et al. |
| 4,848,587 A | 7/1989 | Nipp |
| 4,974,607 A | 12/1990 | Miwa |
| 5,307,263 A | 4/1994 | Brown |
| 5,348,347 A | 9/1994 | Shink |
| 5,371,687 A | 12/1994 | Holmes, II et al. |
| 5,423,404 A | 6/1995 | Shaw |
| 5,594,906 A | 1/1997 | Holmes, II et al. |
| 5,678,571 A | 10/1997 | Brown |
| 5,730,654 A | 3/1998 | Brown |
| 5,832,448 A | 11/1998 | Brown |
| 5,865,314 A | 2/1999 | Jacober |
| 5,897,493 A | 4/1999 | Brown |
| 5,899,855 A | 5/1999 | Brown |
| 5,913,310 A | 6/1999 | Brown |

(List continued on next page.)

FOREIGN PATENT DOCUMENTS

| DE | 196 02 299 A | 7/1997 |
| DE | 197 50 009 C | 9/1999 |
| WO | WO 00/18293 A1 | 4/2000 |
| WO | WO 00/28460 A | 5/2000 |
| WO | WO 00/32098 A1 | 6/2000 |
| WO | WO 00/33236 A1 | 6/2000 |
| WO | WO 01/37174 A1 | 5/2001 |

OTHER PUBLICATIONS

*A Guessing Game to Rally the Diabetic Child*, C. Herold, New York Times, Jul. 26, 2001.

Primary Examiner—Albert K. Wong
(74) Attorney, Agent, or Firm—Alston & Bird LLP

(57) ABSTRACT

A portable storage case for housing a medical monitoring device is provided that facilitates communications with the medical monitoring device while the portable storage case is in transport. The portable storage case may also store the accessories required for the tests and a portable computing device for receiving additional data relating to the various activities of the patient. In order to communicate with the medical monitoring device, the portable storage case may include an integral data connector disposed in a predetermined positional relationship with respect to the medical monitoring device. As such, communication may be established between the integral data connector and a corresponding data connector carried by the medical monitoring device such that data collected by the medical monitoring device may be accessed, such as by being downloaded, once the medical monitoring device is disposed within the case.

31 Claims, 5 Drawing Sheets